United States Patent [19]
Place et al.

[11] Patent Number: 6,113,939
[45] Date of Patent: *Sep. 5, 2000

[54] PHARMACEUTICAL COMPOSITIONS FOR TREATING PRIAPISM AND PEYRONIE'S SYNDROME

[75] Inventors: Virgil A. Place, Kawaihae, Hi.; Robert M. Gale, Los Altos; Randall G. Berggren, Livermore, both of Calif.

[73] Assignee: Vivus, Inc., Mountain View, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/482,366

[22] Filed: Jun. 7, 1995

Related U.S. Application Data

[60] Continuation of application No. 08/093,545, Jul. 19, 1993, Pat. No. 5,474,535, which is a division of application No. 07/787,306, Oct. 30, 1991, Pat. No. 5,242,391, which is a continuation-in-part of application No. PCT/US91/02758, Apr. 22, 1991, and application No. 07/514,397, Apr. 25, 1990, abandoned.

[51] Int. Cl.$^7$ ........................................................ A61F 6/06
[52] U.S. Cl. ................................ 424/430; 424/400; 514/1
[58] Field of Search .................................. 604/60, 19, 48, 604/54, 57, 59, 93, 181, 285, 288; 514/1

[56] References Cited

U.S. PATENT DOCUMENTS

| | | | |
|---|---|---|---|
| 4,784,855 | 11/1988 | Yamashita et al. | 424/436 |
| 5,152,997 | 10/1992 | Ebert et al. | 424/449 |
| 5,236,904 | 8/1993 | Gerstenberg et al. | 424/436 |

FOREIGN PATENT DOCUMENTS

| | | |
|---|---|---|
| 0346297 | 6/1988 | European Pat. Off. . |
| 0266968 | 11/1988 | European Pat. Off. . |
| 2095994 | 10/1985 | United Kingdom . |

OTHER PUBLICATIONS

Schramek et al., 1990, Brit. J. Urol. 65:68–71.
Earle et al., 1990, J. Urol. 143:57–59.
Bertsch et al., 1981, Eur. J. Rheum. Inflam. 4:250–259, see attached abstract.
Molina et al., 1989, J. Urol. 141:1127-8, see attached abstract.
Malloy, T.R., et al., "Pharmacological treatment of impotence", *Urologic Clinics of North America* 14(2):297–305 [see 303–304] (1987).
Klinge, E., et al., "Comparative study of some isolated mammalian smooth muscle effectors of penile erection", *Urol. Res.*, vol. 100:35467 (1977).
Ahmad, S., "Scleroderma and impotence: Response to nitroglycerin applied to the fingers and penis", *South Med. J.* 83:1495 (1990).
Talley, J.D., et al., "Transdermal nitrate, penile erection and spousal headache", *Ann. Intern. Med.* 103:804 (1985).
Yamamura, K., et al., "High–Performance Liquid Chromatographic Assay for Prostaglandin E1 in Various Ointment Vehicles", *J.Chromatography 303*:165–172 (1984).
Sundaram, M.B.M., "Seizures After Intraurethral Instillation of Lidocaine," *Canad. Med. Assn. J. 137*:219–220 (1987).
Negelev, S., "Tropical nitroglycerin: a potential treatment for impotence", *J. Urol.* 143:586 (1990).
Robinette, M.A., et al., "Intracorporal Injection of Papaverine and Phentolamin in the Management of Impotence", *Br. J. Urology 58*:692–695 (1986).
Heaton, J.P.W., et al., "Tropical glyceryltrinitrate causes measurable penile arterial dilation in impotent men.", *J. Urology 143*:729–731 (1990).
Owen, J., et al., "Transcutaneous Nitroglycerine Enhances the Quality of Erections in Impotent Men. Results of a Controlled Trial", *J. Urol.*, 137, 201A, abstract 392 (1987).
Claes, H., et al., "Transcutaneous Nitroglycerin Therapy in the Treatment of Impotence", *Urol. Int.*, 44:309–312 (1989).
Zorgniotti, A.W., et al., "Auto–injection of the Corpus Cavernosum with a Vasoactive Drug Combination for Vasculogenic Impotence" *J. Urol.*, 133:39–41 (1985).
Rudd., et al., *The Pharmacological Basis of Therapeutics*, Gilman et al. (Eds) 7th Ed., Chap. 32 pp. 784–785 (1985).
Turner, J.E., et al., "Prostaglandin $E_2$ in Tylose Gel for Cervical Ripening Before Induction of Labor", *J. Reprod. Med.*, 32(11):815–821 (1987).
Andersson, K.E., et al., "Effects of Prostaglandin $E_2$ Applied Locally on Intravesical and Intraurethral Pressures in Women", *Eur. Urol.*, 4(5):366–369 (1978).
Axelsson, K., et al., "Blood Concentration of Lignocaine after Application of 2% Lignocaine Gel in the Urethra", *Br. J. Urol.*, 55(1):64–68 (1983).
Anonymous, "Intracavernous injections for impotence", *The Medical Letter* 751:39.95 (1987).
Brindley, G.S., "Cavernosal alpha–blockage: A new technique for investigating an treating erectile impotence", *Brit. K. Psychiatr.*, 143:332–377 (1983).
Brindley, G.S., "Pilot experiments on the actions of drugs injected into the human corpus cavernosum penis", *Br. J. Pharmacol*, 87:495–500 (1986).
ISHII, N., et al., "Studies on male sexual impotence. Report 18. Therapeutic trial with prostaglandin E1 for organic impotence", 77:954–962 (1986).
Stackl, W., et al., "Intracavernous injection o prostaglandin E1 in impotent men", *J. Urol.*, 140:66–68 (1988).
Virag, R., "Intracavernous injection of papaverine for erectile failure" [leeter], *Lancet*, 2:938 (1982).

*Primary Examiner*—Laurie Scheiner
*Assistant Examiner*—Jeffrey S. Parkin
*Attorney, Agent, or Firm*—Dianne E. Reed; Reed & Associates

[57] ABSTRACT

A composition for the treatment of impotence via delivery to the urethra comprises a vasoactive prostaglandin and a polyethylene glycol dispersant having sufficient viscosity to be retained without spillage from a urethra receivable insert. The composition can additionally contain an α-blocker. Suppositories can be formulated that are small enough for administration to the male urethra, and that dissolve, melt or bioerode within the urethra to release the active agent(s). The suppositories can contain vasodilators other than prostaglandins as the active for the treatment of impotence. Suppositories can also be formulated that contain active agents useful in the treatment of priapism or Peyronie's syndrome.

6 Claims, 2 Drawing Sheets

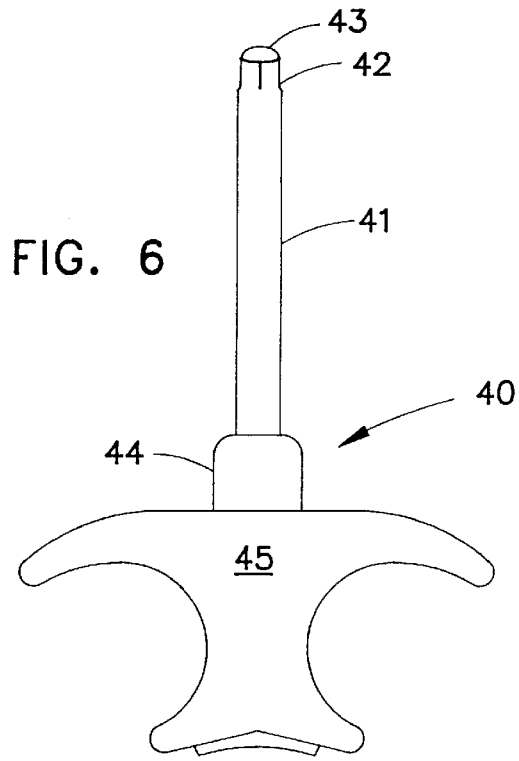
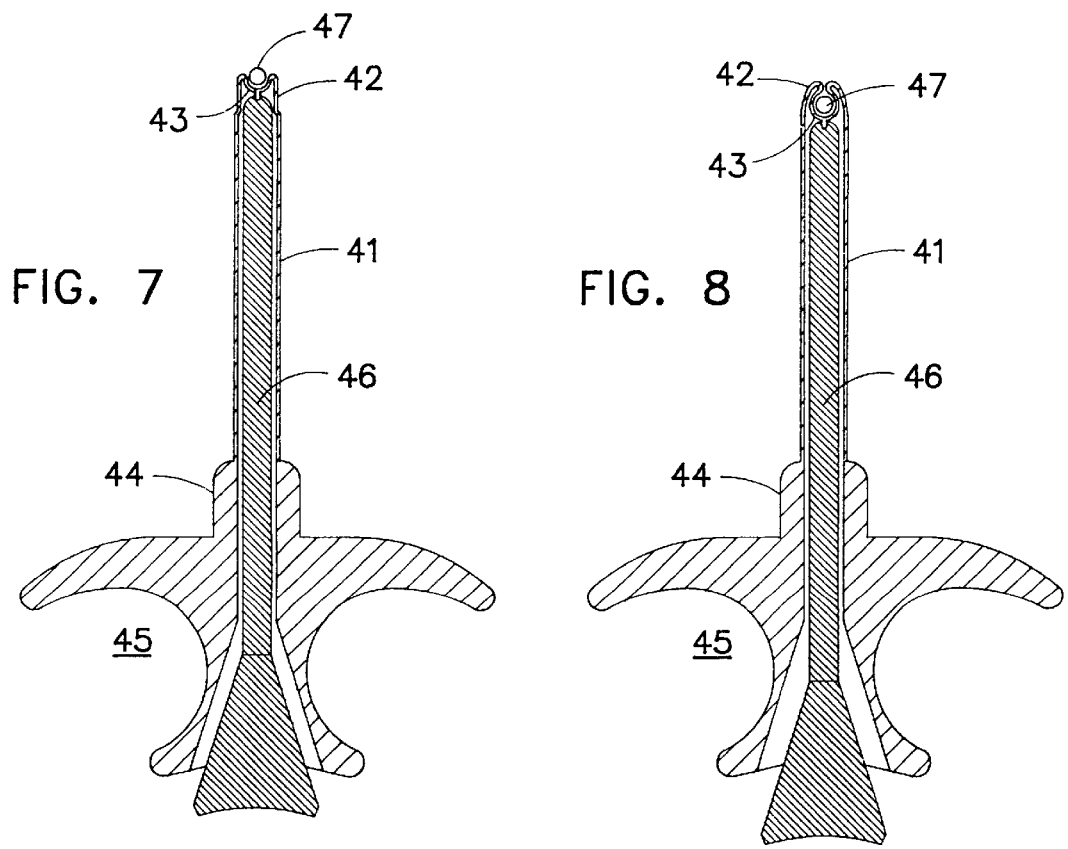

PHARMACEUTICAL COMPOSITIONS FOR TREATING PRIAPISM AND PEYRONIE'S SYNDROME

CROSS-REFERENCE TO RELATED APPLICATIONS

This application is a continuation of U.S. patent application Ser. No. 08/093,545, filed Jul. 19, 1993 and issued as U.S. Pat. No. 5,474,535, which was a divisional of U.S. patent application Ser. No. 07/787,306, filed Oct. 30, 1991 and issued as U.S. Pat. No. 5,242,391, which was a continuation-in-part of both PCT/US91/02758, filed Apr. 22, 1991, and U.S. patent application Ser. No. 07/514,397, filed Apr. 25, 1990, now abandoned.

TECHNICAL FIELD

This invention relates to the treatment of erectile disfunction and more particularly to the treatment of impotence, priapism and Peyronie's syndrome.

BACKGROUND OF THE INVENTION

As used herein, the term "erectile dysfunction" refers to certain disorders of the cavernous tissue of the penis and the associated facia which produce impotence, the inability to attain a sexually functional erection; priapism, the persistent and often painful erection of the penis; and Peyronie's syndrome, a condition characterized by fibrosis of the cavernous tissue and associated painful and distorted erection of the penis. Erectile dysfunctions, particularly impotence, affect a substantial number of patients. For example, impotence is estimated to affect approximately 10 million American men and can result from any of numerous physiological or psychological factors which cause the blood flow to and from the penis to remain in balance thereby preventing retention of sufficient blood to cause rigid dilation of the corpus cavernosa and spongiosa. As used herein, the term "impotence" is used in its broadest sense as the inability to attain a sexually functional erection when desired.

Treatments for impotence include psychosexual therapy, hormonal therapy, administration of vasodilators such as nitroglycerin and $\alpha$-adrenergic blocking agents (hereafter "$\alpha$-blockers"), vascular surgery, implanted penile prostheses, vacuum devices and external aids such as penile splints to support the penis or penile constricting rings to alter the flow of blood through the penis. See Robert J. Krause, et al., Impotence, N. Eng. J. Med. Vol. 321, No. 24, Dec. 14, 1989 for a general discussion of the current state of the art.

Originally Dr. Latorre and later Dr. R. Verag of Paris demonstrated that impotence could be physiologically treated by the direct injection of a vasoactive drug into a patient's epigastric artery and thereafter thousands of patients have treated their impotence by self injection of such drugs directly into the corpora cavernosa. Forward, I$^{er}$ Symposium International Sur L'Erection Pharmacologigue, Nov. 17–19, 1989, Paris, p 2; R. Virag, et al, *Intracavernous Injection of Papaverine as a Diagnostic and Therapeutic Method in Erectile Failure*, Angiology, 35, pp 79–87, 1984; (See also, U.S. Pat. Nos. 4,127,118, 4,766,889 and 4,857, 059 which are incorporated herein by reference). The drugs most commonly used include $\alpha$-blockers, such as the long acting phenoxybenzamine and the short acting phentolamine, smooth muscle relaxants such as papaverine, prostaglandins having a vasoactive function such as prostaglandin-E$_1$ (PGE$_1$) and combinations of such drugs having different receptor effects to enhance therapy. Erection producing intracavernous injection doses of papaverine are typically in the range of about 7.5 to 160 mg, of phentolamine are in the range of about 0.1 to 10 mg of and of PGE$_1$ are in the range of about 2.5 to 50 micrograms. See for example, Kurkle, et al, *Injection Therapy for Impotence* Urol. Clin. of America, Vol. 15, No. 4, November 88, pp 625–629 and N. Ishii, et al, *Intra Cavernous Injection of Prostaglandin E for the Treatment of Erectile Impotence*, J. of Urol., Vol. 141, February 1989, pp 323–325. Vasoactive intestinal peptides at doses of 10–100 $\mu$g have also been reported as producing erection on intracavernous injection. See also, H. Handelsman, *Diagnosis and Treatment of Impotence*, U.S. Dept. of Health Services, Agency for Health Care Policy and Research, April 1990, for a summary of intracavernal injection and other treatment of impotence.

Although intracavernous injection of vasoactive drugs can produce a relatively rapid onset of erection in patients suffering from impotence attributable to venous leakage or arterial insufficiency; patients often find the injections psychologically disturbing, painful, traumatic or inconvenient as evidenced by a high discontinuance rate. See S. Althouf, et al, *Why Do So Many People Drop Out From Auto-Injection Therapy for Impotence?*, Journal of Sex & Marital Therapy, Vol. 15, No. 2, 1989, pp 121–129. Adverse side effects including priapism, corporeal nodules and diffuse fibrosis, drug tolerance, bruising and hematomas. Swelling and ulceration of penile skin at the injection site have also been reported.

Nevertheless, because of the relatively innocuous intervention involved and the high failure rate of penile prostheses, the pharmacological approach to the treatment of impotence is still quite advantageous to a large number of patients and could be even more so if the side effects could be avoided. The administration of vasodilators via the male urethra has been disclosed in Voss, U.S. Pat. No. 4,801,587 and Kock, EPA 0357581 to produce erections as has the transurethral administration of testosterone, S. M. Milco, *Bulletins et Memoirs de la Societa Roumaine D'Endocrinologie*, Vol. 5, pp 434–437 (December 1939), strychnine and another drug (citation to be provided). It has also been suggested that cocaine administered transurethrally could contribute to an erection although the reported side effects were catastrophic, JAMA, Vol. 259, No. 21, page 3176 (1988).

Priapism is less common than impotence and can be attributed to various causes. It has been associated with diseases producing intravascular agglutination or sludging, such as leukemia, and pharmacological priapism has been reported in a small percentage of patients who are treated for impotence by intracavernous injection. Priapism has been treated by intracavernous injection of vasoconstrictors such as $\alpha$-adrenergic receptor agonists (hereafter "$\alpha$-agonist"). The reported effective doses of the $\alpha$-agonist, phenylephrine, are in the range of about 0.1 to 2 mg.

Peyronie's syndrome is a condition of unknown etiology characterized by fibrosis of the cavernous tissues and painful and distorted erections. The current treatment consists of injection of steroids and other anti-inflammatory agents into the site of the fibrosis.

With respect to administration of drugs directly to the penis, medicated catheters such as described in U.S. Pat. No. 4,640,912 have been used to prevent or treat localized infections and irritation of the urethra and bladder; a nitroglycerin coated, erection inducing condom is disclosed in U.S. Pat. No. 4,829,991; the transurethral administration of certain drugs is suggested in U.S. Pat. Nos. 4,478,822, 4,610,868, 4,640,912 and 4,746,508; and medicated urethral suppositories, inserts or plugs, typically containing anti-infective agents or spermicides are disclosed in U.S. Pat. Nos. 1,897,423, 2,584,166, 2,696,209 and 3,373,746, for example. As noted above, Voss, Kock, Milco, and others disclose introducing agents into the urethra to induce erections.

According to our invention, we have provided methods and dosage forms for the treatment of erectile dysfunctions which are painless, capable of rapidly, safely and effectively producing erection of the penis in the case of impotence, detumescence of the penis in the case of priapism and administration of anti-inflammatory drugs to fibrotic sites in the case of Peyronie's syndrome without the above described adverse side effects and with a high degree of patient acceptability.

BRIEF DESCRIPTION OF THE INVENTION

We have found that the above-described erectile dysfunctions can be safely and effectively treated by the transurethral administration of the appropriate therapeutic drug or combination of therapeutic drugs (as used herein the term "agent" refers to a drug or a combination of drugs capable of producing the desired therapeutic effect) and have provided compositions and penile inserts adapted to be easily and painlessly inserted into the urethra, which compositions or inserts carry the appropriate therapeutic agent in an amount sufficient to produce the desired result.

In one preferred embodiment of this invention the therapeutic agent is applied as a coating on a penile insert configured to prevent complete insertion and to facilitate removal.

In another preferred embodiment of this invention, the agent is contained in a gel, cream, ointment or suppository for example which may be deposited in the urethra from a specially designed inserter.

BRIEF DESCRIPTION OF THE DRAWINGS

This invention and the advantages thereof will be readily apparent from the following description of the invention with reference to the accompanying drawings wherein:

FIG. 6 is a side view of another inserter construction for introducing a dose into the urethra;

FIG. 7 is a cross-section through the inserter of FIG. 6 in the filling position; and FIG. 8 is a cross-section through the inserter of FIG. 6 in the loaded position.

Figure 1:
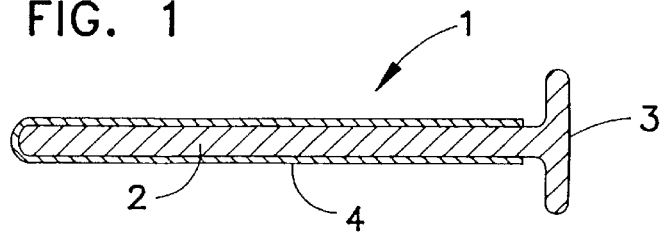
FIG. 1 is a cross sectional view of one embodiment of this invention.

DESCRIPTION OF THE INVENTION
INCLUDING THE BEST MODE

In its broadest aspect, this invention contemplates the treatment of erectile dysfunction by the transurethral administration of an agent, therapeutically effective with respect to the dysfunction, directly into the blood supplying the corpus cavernosum via the cross circulation with the spongiosa surrounding the urethra. The erectile dysfunctions which may be so treated include impotence, for which the therapeutic agent is one or more drugs capable of producing a vaso-dilatory or other erection inducing effect. Suitable vaso-dilatory agents include nitrates such as nitroglycerin and isosorbide dinitrate, long and short acting α-blockers such as phenoxybenzamine, dibenamine, doxazosin, terazosin, phentolamine, tolazoline, prazosin and trimazosin; adenosine, ergot alkaloids, chlorpromazine, haloperidol, yohimbine, verapamil and other calcium blockers, natural and synthetic vasoactive prostaglandins and analogs thereof such as $PGE_1$, including alprostadil, misoprostol and enprostil, for example, prostaglandin $E_2$, minoxidil, vasoactive intestinal peptides or any other agent which is capable of producing an erection when administered transurethrally. For example, dopamine agonists such as apomorphine and bromocriptine, testosterone, cocaine, strychnine, and opioid antagonists such as naltrexone have been reported to induce erection and they may also be useful according to this invention. See S. Lal et al, *Apomorphine: Clinical Studies on Erectile Impotence and Yawning*, Prog. Neuro-Psychopharmacology, Vol. 13, 1989, pp 329–339 and A. Fabbri et al, *Endorphins in Male Impotence, Evidence for Naltrexone Stimulation of Erectile Activity in Patient Therapy*, Psychoneuroendocrinology, Vol. 14, No. 1 & 2, pp 89, 103–111.

We have found that combinations of two or more drugs can exhibit a synergistic effect and preferred combinations are combinations of α-blockers and prostaglandin particularly prazosin, doxazosin or terazosin with $PGE_1$, such as alprostadil, misoprostol or enprostil.

With respect to priapism, the therapeutic agent may be one or more vasoconstrictor drugs. Suitable vasoconstrictors include α-receptor agonists such as epinephrin, phenylethylamine, norepinephrine, dopamine, metaraminol, phenylephrine, methoxamine, ephedrine, phenylpropanolamine, mephentermine and propylhexedrine, for example, β-blockers such as butoxamine, dichloroisoproterenol, propranolol, alprenolol, bunolol, nadolol, oxprenolol, penbutolol, pindolol, sotalol, timolol, metoprolol, atenolol, acebutolol, bevantolol, pafenolol, and tolamolol, for example, and any other agent which is capable of producing a detumescent effect when applied transurethrally.

With respect to Peyronie's syndrome, the therapeutic agent may be one or more anti-inflammatory drugs such as corticosteroids including cortisone, hydrocortisone, tetrahydrocortisone, prednisone, prednisolone, methylprednisolone, fludrocortisone, desoxycortisol, corticosterone, triamcinolone, paramethasone, betamethasone, dexamethasone and beclomethasone, for example, non-steroidal anti-inflammatories such as salicylic acid, aspirin, diflunisal, methyl salicylate, phenylbutazone, oxyphenbutazone, apazone, phenacetin, acetaminophen, indomethacin, sulindac, mefenamic acid, meclofenamate sodium, tolmetin, ibuprofen, naproxen and fenoprofen, for example, and other drugs such as testosterone which may be capable of producing an anti-inflammatory effect on fibrous tissue within the corpus cavernosum when administered transurethrally.

It is preferred that the agent be rapidly delivered through the urethra in order to bring about a rapid onset of the desired effect. To that end the agent containing material may be caused to contact the urethra along a sizable portion, about 2–3 cm, of its length rather than localizing it at one site along the urethra. Also, the agent should be applied at least 1 cm into the penis and past the point where the transition from the epidermal character of the glans has been completed. It has been found that rapid absorption can also be obtained when a small, rapidly releasing dosage form such as a gel, cream, ointment or suppository or a coating is deposited between the proximal portion of the fossa navicularis including the valves of navicularis and the distal portion of the pendulous urethra. This appears to be the optimum location for rapid absorption of the agent and although it varies from individual to individual it is generally at a depth of 2–5 cm in the penis.

In all of the dosage forms contemplated herein, it is desirable that the volume of agent-containing material that is deposited in the urethra remain within the urethra and in contact with the wall of the urethra until complete absorption of the agent has occurred and that the material be deposited in a manner that permits relatively rapid absorption of the agent. Dosages in the range of 50–100 mg (approximately 50–100 μl in liquid volume) tended to exhibit observable spillage prior to complete absorption. Accordingly, the amount of drug-containing material retained in the urethra should be less than about 100 mg and preferably less than about 50 mg. Adequate lubrication has been obtained with as little as 5–10 μl of lubricating carriers such as polyethylene glycol (PEG) 1000 and 1450.

The dose of agent can be contained in any of the fluid or semi-fluid solutions, suspensions, dispersions, ointments, pastes or gels selected from the numerous formulations of such types known to the art but preferably comprises a formulation in which the agent is dispersed in a pharmaceutically acceptable carrier which rapidly releases the agent within the urethra. These formulations can also contain pharmaceutically acceptable antioxidants such as BHT, for example, and other stabilizing agents as is known to the art as may be required to extend shelf life.

Figure 3:
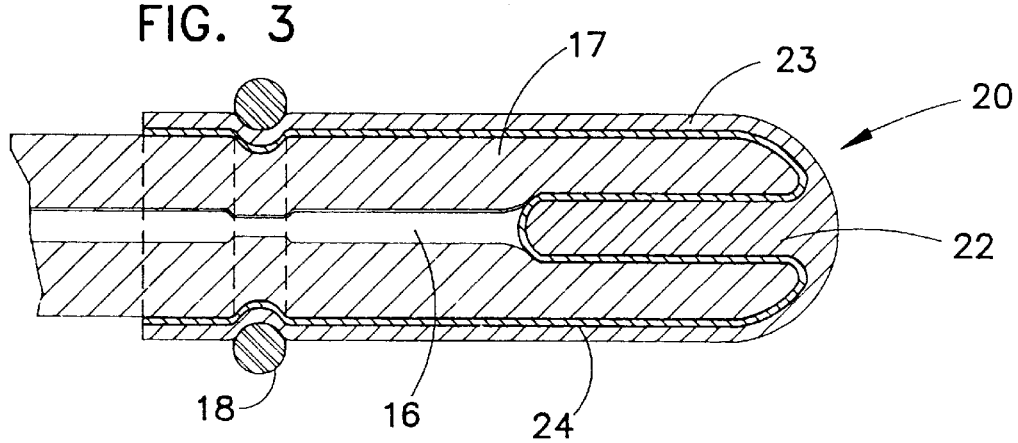
FIG. 3 is an exploded view of a penile insert according to the invention and its container.

Such a dose can be easily introduced into the urethra from a flexible tube, squeeze bottle, pump or aerosol spray single or multiple dose administrator, for example. The agent may also be contained in rapidly releasing coatings or suppositories which are rapidly dissolved absorbed, melted or bioeroded in the urethra. Urethral permeation enhancers for the agent may also be included in the agent containing compositions. In certain embodiments which are illustrated in FIGS. 1 and 3, the agent is included in a coating on the exterior surface of a penile insert.

In the presently preferred embodiments of the invention, the agent is contained in a dose of predetermined volume which is deposited as a suppository into the urethra at the desired location.

Referring now to FIG. 1, a penile insert 1 comprises a shaft portion 2 which is sized to be easily and comfortably inserted into the male urethra. Means are also provided to prevent complete insertion of the inserter into the urethra in a manner that would make removal difficult. The means may simply be a portion of the shaft of adequate length to be gripped and not released during use. It is preferable however that the end of shaft 2 is provided with an enlarged terminal portion 3 configured to prevent complete insertion into the urethra and to facilitate removal of the device after the agent has been delivered. The internal end of shaft portion 2 is preferably provided with a rounded, blunted end to prevent discomfort on insertion and is typically from about 3 to 5 millimeters in diameter and from about 2 to 12 centimeters in length.

The insert itself may be made from any pharmacologically acceptable material and although it may be rigid, it is preferred that the device be relatively soft and flexible for purposes of comfort, merely having sufficient rigidity to facilitate insertion. For this purpose various pharmaceutically acceptable natural or synthetic rubber or polymeric materials such as natural rubber, silicone rubber, ethylene vinyl acetate (EVA) copolymers, polyethylene, polypropylene, polycarbonate, polyester, polyurethane, polyisobutylene polymers, and polyoxyethylene polymers such as Delrin® manufactured by Du Pont, for example, are suitable. Polypropylene is particularly useful, especially where the product is to be radiation sterilized.

Although the therapeutic agent and optionally a permeation enhancer may be dispersed throughout the body of the insert 1, it is preferable that the agent be concentrated on the urethra-contacting surfaces of the device in order to permit rapid absorption of the agent and any permeation enhancer. As shown in FIG. 1, the shaft portion 2 of the insert 1 is provided with an agent-containing coating 4 which comprises the desired agent dose and, if used, a permeation enhancer, dispersed throughout a rapidly releasing carrier. The coating 4 may be applied to the insert by means of dip coating in an appropriate agent-containing bath, spray coating, heat melt coating, evaporation of a fixed volume of a solution or suspension of the agent in a volatile vehicle or by co-extrusion of an agent-containing layer onto the surface of shaft 2, for example.

To facilitate insertion, coating 4 preferably has lubricating properties and may contain dispersant materials such as PEG, propylene glycol, glycerine, polyvinyl pyrrolidine (PVP), polyvinyl alcohol (PVA), hydroxy alkyl celluloses or cyclodextrins, for example, which are or become slippery upon insertion into the urethra. Materials such as glycerol monolaurate, polyethylene glycol monolaurate, and glycerol monolaurate, for example, may combine permeation enhancing properties with lubricating properties.

To facilitate adherence of the drug coatings to the penile insert, the surfaces to which the coatings are applied may be slightly roughened. Also, to provide a visual indication of complete agent release, the coating, instead of being clear and transparent, can be selected to provide a different visual appearance from that of the uncoated insert. This can be accomplished with the use of dyes or pigments or can be a property of the agent or coating material itself.

In use, the device would be inserted slowly (about 5–10 seconds) into the urethra up to the terminal portion 3 and either maintained in place until the agent is absorbed (about 30–45 seconds) and then slowly removed, or more preferably, particularly with shorter devices (about 2–5 cm in length), the device 1 would be inserted into the urethra up to portion 3 and then, while compressing the penis around shaft 2, gently but firmly rotated and reciprocated to wipe all the agent-containing material from the surface of the device prior to removal.

When the agent dose is formed from a water soluble material such as PEG it is also preferable that the patient urinate shortly before administration of the dose. The residual urine in the urethra cause the dose to dissolve more rapidly producing more rapid drug absorption.

Figure 2:
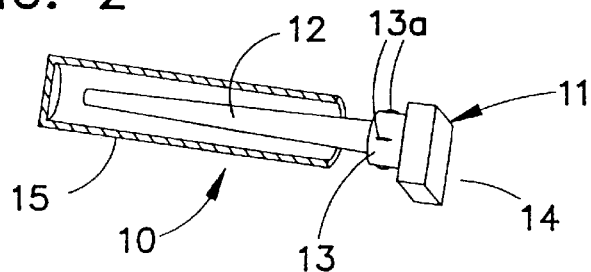
FIG. 2 is a cross sectional view of another embodiment of this invention.

Referring now to FIG. 2, a combination insert/container 10 is shown in which the insert 11 is provided with a tapered agent-carrying shaft portion 12 which terminates in a plug portion 13 which may also be provided with sealing ridges 13a. Plug element 13 terminates in cap portion 14 which may be larger than plug 13 and preferably of a square or other polygonal configuration to make it easy to rotate insert 11 for removal from its container 15. Container 15 is generally tubular in shape closed at one end and of sufficient length to receive the insert up to contact with cap 14. The interior diameter of container 15 and the exterior diameter of plug 13 with sealing ridges 13a are selected to provide a sliding seal that is sufficient to prevent insert 1 from falling out of the container and the passage of contaminants into the container while permitting removal of the insert with the application of a reasonable force on cap 14.

Referring now to FIG. 3, another embodiment of the invention is shown in which the penile insert 20 comprises a shaft portion 22 adapted to be received within the male urethra and a terminal portion 23 in the form of a tubular cap adapted to enclose the glans and, if more agent delivering surface is required, some portion of the shaft of penis 17. The body-contacting surface of insert 20 is provided with an agent-containing coating 24 similar to that described with respect to FIG. 1 which coating is applied to the shaft 22 and such other portion of the interior of the terminal portion 23 as is desired. The embodiment of FIG. 3 may be used with respect to less potent agents which require an administration rate greater than can be obtained directly through the urethra. Thus the portion of the coating 24 which contacts the glans and the shaft of the penis also provides for the administration of the agent directly through the skin of the penis in addition to the transurethral administration.

In use, the device would be inserted into the urethra 16 and in contact with the skin of penis 17 and maintained in place until all the agent has been released from coating 14. In FIG. 3 a constrictive, typically elastic, band 18 is applied around the base of the penis 17 while the insert 20 is in place to constrict the penis and prevent the flow of blood therefrom. This constrictive band can also be used with respect to the embodiments of FIGS. 1, 2, 4 and 5. It is useful in impotence where it will prevent the flow of blood from corpus cavernosum thereby assisting in the maintenance of the erection and in Peyronie's syndrome where it will cause the anti-inflammatory drug to remain in the corpus cavernosum for an extended period of time. The constricting bands would not normally be used when the device of this invention is used to treat Priapism where it is desired to increase, rather than retard, the flow of blood from the penis.

In the practice of this invention it is desirable that the entire dose of the agent be reproducibly deposited in contact with the urethra at the desired location within the urethra. Because the coatings on the inserts of FIGS. 1–3 are in contact with the urethra during the insertion and removal procedure, it is possible that some of the coating may be deposited at non-optimum locations or that all of the coating may not be removed prior to withdrawal of the insert. In order to obtain a more precise control of the dose administered and the site of application, the dose can be contained within the insert where it is protected from contact with the urethra during insertion and means can be provided to positively displace the entire dose from the insert into the urethra at the desired depth of application.

Figure 4:
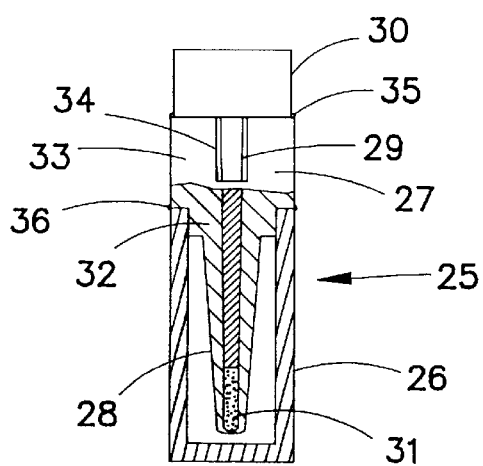
FIG. 4 is a side view, partly in section, of an inserter/container assembly for introducing a composition containing a dose of agent into the urethra.
Figure 5:
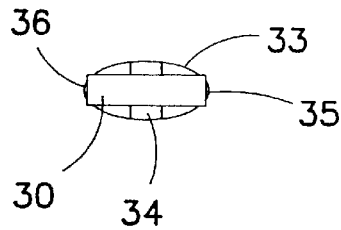
FIG. 5 is a top view of the inserter/container of FIG. 4.

Referring now to FIGS. 4 and 5 another embodiment of this invention is shown for use when the agent is contained in an ointment, paste, suppository, cream or gel formulation of the type described above rather than as a coating on the shaft of an inserter. The dosage inserter/container 25 comprises a container 26 closed at one end and receiving inserter 27 in the other end. Although container 26 can be cylindrical in configuration it is preferred to form container 26 into a more volume efficient flattened configuration such as elliptical or rectangular because there is no need to maintain a large clearance between the exterior of inserter 27 and the interior of container 26, to prevent inadvertent removal of any coating on inserter 27. Inserter 27 comprises a shaft portion 28 having an external configuration similar to that of the inserter shown in FIGS. 1 and 2 but provided with a longitudinal bore which receives the piston portion 29 of plunger 30, the agent-containing dose 31 in the form of an ointment, paste, suppository, cream or gel having sufficient viscosity to enable it to remain, without spillage, within the cavity formed between the tip of piston 29 and the end of the bore. The bore may communicate with the urethra through the single outlet shown in FIG. 4 through which the dose is ejected by movement of piston 29. Alternatively, the end of the inserter could be provided with a multiplicity of small holes distributed about the tip through which the dose could be extruded in small streams into contact with the urethra.

Preferably, means are provided to prevent unintentional activation of plunger 30 which in its simplest form could be a frangible bead or bond which resists relative motion of plunger 30 with respect to shaft portion 28 until a predetermined force is applied. A more positive means is illustrated in FIGS. 4 and 5 wherein shaft portion 28 terminates in a plug portion 32 configured to form a sliding seal with the interior of container 26. The plug portion 32 terminates in cap portion 33 provided with receptacle means 34 configured to receive plunger 30 when plunger 30 is in a first position and to be incapable of receiving plunger 30 when in a second position and being of sufficient depth to allow displacement of piston 29 over sufficient travel to fully displace dose 31 from the inserter. In FIGS. 4 and 5 the receptacle 34 is shown as a slot across cap 33. Plunger 30 is mounted transverse to slot 34 and maintained in this first position by a frangible bond 35. Cap 33 is likewise sealed to container 26 by a similar frangible bond 36. These frangible bonds can be formed by any suitable technique which include adhesive bonding, heat or sonic welding or the application of some form of "shrink wrap" material, for example.

This configuration is readily adaptable to automated filling together with precise control of the quantity of dose 31 and provides for positive administration of the desired quantity of agent at the desired site of application.

Prior to use the device is protected from inadvertent displacement of dose 31 by means of the frangible seal 35 and inadvertent removal of the inserter by means of frangible seal 36. In use, frangible seal 35 would be broken by rotating plunger 30 from its first position to a second position where it is in alignment with receptacle 34 and frangible seal 36 would be broken to remove the inserter 27 from container 26. The inserter would then be placed into the urethra to the depth of plug 32 and plunger 30 depressed into receptacle 34 to completely eject dose 31 into the urethra at the desired point of application. The inserter 27 would then be removed leaving the dose 31 within the urethra.

The materials used to form the inserter/container 25 are the same as those which can be used in fabricating the devices of FIGS. 1 and 2 for example and when these materials are thermoplastic the formation of the frangible bonds 35 and 36 by sonic fusion is a preferred technique.

In order to assure the complete displacement of dose 31 by piston 29, relatively precise tolerances must be maintained with respect to the internal and external diameters of the bore through shaft portion 28 and of the piston 29, respectively. FIGS. 6, 7 and 8 describe a device in which manufacturing tolerances can be more relaxed while still maintaining positive displacement of the entire dose to the urethra at the desired position. Inserter 40 of FIGS. 6, 7 and 8 comprises a sleeve 41 which is preferably slightly thinner or otherwise weakened about the periphery of its distal end 42 such that this portion is more flexible than the remainder of sleeve 41 so that it will deform preferentially at this location. Sleeve 41 is also preferably provided with a thickened terminal portion 43. Sleeve 41 is sized to be received within the male urethra and preferably terminates at a shoulder 44 on handle 45, shoulder 44 being of sufficient diameter to prevent insertion into the urethra. Sleeve 41 may be formed as a unit with handle 45 or it may be formed separately and bonded or otherwise attached to shoulder 44. Handle 45 is provided with a central bore having a diameter corresponding to the interior of sleeve 41 and piston 46 is slidably received within sleeve 41 and handle 45. The distal end of piston 46 is firmly connected to the interior portion of the end portion 43 of sleeve 41. When piston 46 is moved to a position where it completely fills sleeve 42, the inserter has the configuration shown in FIG. 6. However, when piston 46 is withdrawn slightly from the position of FIG. 6, the end 43 of sleeve 41 will be withdrawn with the piston to form a cup shaped cavity into which a suppository 47, preferably spherical, comprising the agent dose can be received. Upon further withdrawal to the position shown in FIG. 8, the peripheral portion 42 of the end of sleeve 41 will have been withdrawn by piston 46 into the sleeve 41 causing it to surround and envelope suppository 47.

In operation, the spherical suppositories 47 would be fabricated in the frozen condition by any of the conventional techniques used for the manufacture of spherical granules of predetermined size. Equipment for manufacturing small spherical particles is known to the art and includes rotary processing, multiple-step extrusion and spheronization equipment. Suitable equipment is available, for example, from Niro-Aeromatic, Inc. of Colombia, Md.

To load the inserter, piston 46 would be moved to the position shown in FIG. 7 and the frozen suppository 47 deposited in the cup shape receptacle so formed. The piston 46 would then be withdrawn to the position shown in FIG. 8 completely enclosing and enveloping the suppository 47 within the retroverted tip 42 of the sleeve. In use, the loaded inserter would be inserted into the male urethra until shoulder 44 abuts the meatus and plunger 46 moved forward to the position shown in FIG. 6 thereby releasing suppository 47 from the tip of the inserter and depositing it at the desired depth.

Inserter 40 may be made from any of the materials described in connection with the embodiments of FIGS. 1–4 and may be provided with means for preventing inadvertent actuation as described with respect to FIGS. 4 and 5. For example, after the inserter is loaded with the suppository as shown in FIG. 8, sonic bonds could be formed between the handle 45 and the piston 46 or a cap-like structure similar to that of FIGS. 4 and 5 could be employed.

Although the configurations shown in FIGS. 4–8 are preferred configurations, other inserter/container configurations can be used and any mechanism by which a predetermined quantity of drug can be introduced from the inserter at a predetermined depth in the urethra is suitable for use with this invention. As with the other devices of this invention, the agent in dose 31 can be one or more drugs. However, when a combination of drugs is required to produce the desired therapeutic effect, it is also possible to sequentially administer separate doses of each individual drug, each of which can then be titrated by the physician and/or patient to produce the desired effect.

The embodiments of this invention can either be manufactured under sterile conditions thereby eliminating the need for post manufacturing sterilization or they can be manufactured under non-sterile conditions and then subsequently sterilized by any suitable technique such as radiation sterilization.

The penile inserts and injectors of this invention can be manufactured by typical plastic forming and coating process and solvent evaporation known to the art which include molding, extrusion, heat forming, dip coating, spray coating, heat melt coating and solvent evaporation. Although prototype devices of FIG. 1 were made from EVA rods which were heat formed by hand into the configuration of FIG. 1 on a hot plate to flatten the exterior end and blunt the interior end, components forming the various embodiments of this invention can be made in quantity in conventional injection molding equipment.

Molded parts which require coating can be coated by any suitable process. Dip coating, with control of the temperature and viscosity of the bath and the dwell time of the article to be coated in the bath, coupled with air wiping for added precision is capable of producing quite reproducible coatings within the requirements of this invention. Depositing a known volume of a solution or suspension of the agent/dispersant in a volatile carrier onto the shaft in the presence of a warm air stream also produces coating in a reproducible manner as does the application of a known volume of a melt containing the agent to a cool inserter shaft.

PEG based coating and suppository formulations are particularly suitable to this invention because they are solid at refrigerator or ambient temperatures, have lubricating properties, dissolve in the urethra to allow rapid absorption of the active agent therein dispersed and some lower molecular weight PEGs also melt at urethral temperatures.

PEGs of varying molecular weight from about 400–8000 including mixtures of PEG can be used according to this invention. All PEGs will dissolve in the urethra whereas only the lower molecular weight species will melt. Temperatures in the flacid penis are normally in the range of 30–32° C., at or above the melting point of PEGs up to about molecular weights of 600. PEG 1000 melts at about 37–40° C. PEG 1450 melts at about 43–46° C. and higher molecular weight PEGs melt at higher temperatures. PEGs as a class, are highly water soluble, about 70–80% by weight in water at 20° C. and even higher at the temperatures within the urethra.

At 70° C. the viscosity of a 50—50 blend of PEG 1450 and PEG 400 is such that approximately 100 mg of a dip mixture was reproducibly left on a 10 cm long by 3.5 mm diameter EVA rod after a single dip. By varying the molecular weight of the PEGs and/or their ratios and/or the temperature of the bath, the viscosity of the bath and the resultant weight of the coating can be adjusted. For example, a 1:2 weight ratio mixture of PEG 600 and PEG 1000 will have a melting point of about 32° C. and could be expected to yield a coating of approximately 50 mg at a bath temperature within the range of about 50–80° C.

PEG 1450 is available as a flake material at room temperature which on melting and cooling forms a smooth coating on the insert of this invention. At bath temperatures in the range of 60° C. to 80° C. coatings of about 50 mg can be obtained from a single dip.

As another example, at 70° C., PEG 1450 deposited on the 2 cm of the tip equals about 50 mg. The slower dissolution of the higher molecular weight PEG allows controlled deposit on a limited area. As the system is inserted into the urethra the slower melt of PEG 1450 allows minimal deposition in the distal urethra and maximum at the depth of full insertion.

Doses such as coatings and suppositories formed from the lower molecular weight PEGs need to be stored under refrigeration when high ambient temperatures are anticipated. Doses formed from PEG 1450 and above, however, have physical stability even when carried exposed to high summer temperatures.

Another approach to forming the desired coating on the shaft 12 of the inserter is to micropipette a known quantity of the agent and dispersant in solution or suspension in a volatile solvent onto the shaft 12 which is maintained in a downwardly inclined position in the presence of a warm air stream to permit rapid evaporation of the solvent before any of the liquid can drop from the shaft. This approach is particularly suitable when both the agent and the dispersant are mutually soluble in the volatile carrier.

As an example, $PGE_1$ together with a lubricating dispersant such as propylene glycol, PEG, glycerin, PVP, PVA, cyclodextrin or hydroxyalkyl cellulose for example, would be dissolved in weight ratios of dispersant to agent of 1:1–10:1 in alcohol at a concentration such that a small volume, approximately 10 μl for example, of the alcoholic solution contains the desired dose of the agent. This predetermined quantity of solution would be introduced from a micropipette onto the surface of the inserter in the presence of a warm air stream and would evaporate rapidly to form the desired coating. The volume of solution is not critical but should be selected based on the size of the insert and the viscosity of the solution such that a relatively even coating of the solvent solution on the shaft is obtained without any spillage prior to evaporation of the volatile solvent. Melted $PGE_1$ containing the agent can also be micropipetted in a similar manner onto a cool inserter shaft to provide reproducible doses of single or multiple drugs.

Preferably, the total weight of the dose should be minimized consistent with the maintenance of lubricating properties. At about the 50–100 mg level, the capacity of the urethra to receive and retain the agent containing dose and rapidly absorb the agent appears to be reached as some spillage of the dose was observed. Accordingly, dose weights should be less than about 100 mg and preferably less than about 50 mg. Similar amounts are contemplated whether the dose is in the form of a coating or is in the form of a solution, dispersion, ointment, paste, gel or suppository, for example.

Once the weight of the agent-containing dose or coating has been selected, the concentration of the agent in the carrier would be appropriately selected to provide the desired total dose within the dosage form or coating.

Unit dosages for $PGE_1$ are in the range of about 10 to 2000 μg, about 50 to 500 μg being preferred, the unit dosages of papaverine are in the range of about 1–50 mg, and the unit dosages of phentolamine are in the range of about 1–10 mg, and the unit dose of prazosin, doxazosin and terazosin are in the range of about 50–2000 μg per dose with 100 to 1000 μg being preferred. It has been observed that combinations of two or more drugs such as $PGE_1$ ie, alprostadil, misoprostol or enprostil with α-blockers, ie, prazosin, doxazosin or terazosin tend to potentiate the erectile effect thereby permitting efficacy to be obtained at lower doses of both drugs.

If the agent is a combination of drugs they all may be included in one dosage form. However, when the agent comprises more than one drug, it would be preferable to sequentially administer each drug from a dosage form containing only one drug.

It is always preferred to use the lowest effective dose in any medical intervention and it is contemplated that the dosage forms of this invention would be provided in various, incremental doses. The patient would initially titrate himself to the dosage effective for him by using the lowest dosage, and repeating administration until the desired effect is obtained. Thereafter the patient would select an effective incremental dosage that is close to the determined higher dosage or could continue using multiple lower doses.

The following examples of this invention are provided.

EXAMPLE 1

A 3.5 mm EVA (28% VA) rod was formed into an insert having a shaft approximately 10 cm long with a spherical, blunted tip and a head portion approximately 4 mm thick and 1 cm in diameter on a hot plate. A dipping bath comprising a 50—50 weight blend of PEG 1450 and PEG 400 and sufficient agent to attain the desired concentration in 100 mg of coating was prepared and heated to 70° C. The insert suspended by its head, was dipped into the dipping bath and removed.

The total weight of the coating so obtained was approximately 100 mg. Nine inserts having coatings containing approximately 50 μg of $PGE_1$ and nine inserts having coatings containing approximately 50 μg $PGE_1$ and 100 μg prazosin hydrochloride were prepared. When used by an impotent human volunteer, four doses of the 50 μg $PGE_1$ were required to achieve minimal erection. The dosage forms combining $PGE_1$ and prazosin produced a stronger erection in both normal and impotent volunteers at a lower total dose of two units in a shorter period of time. A slight burning sensation in the urethra was observed by the normal volunteer with the devices using the prazosin hydrochloride but not by the impotent patient. The use of the base form of prazosin rather than the hydrochloride may eliminate the sensation.

EXAMPLE 2

A 3 mm diameter EVA (24% VA) rod approximately 10 cm in length was blunted and rounded on one end and flattened on the other by manipulation on a hot plate. A gelled aqueous coating formulation, comprising 9 gm of 95% ethanol, 1 gm of propylene glycol, 0.2 gm of hydroxypropyl cellulose and 2 mg of $PGE_1$ was prepared and dip coated on the shaft of the rod to a total loading of about 500 mg. The residual ethanol in the coated rod was allowed to evaporate. It is estimated that the loading of $PGE_1$ was about 200 μg/unit. Penile erection was produced in a normal human subject within ten minutes after the sequential insertion of two rods into the urethra for a total $PGE_1$ dose of 400 μg.

EXAMPLE 3

A 3.5 mm EVA (28% VA) rod approximately 10 cm long with rounded tip and flattened head is coated with 500 μg of prazosin base in a PEG blend (1:2 PEG 600:PEG 1000) having a melting point of approximately 32° C. Initial tumescence should be achieved within several minutes after insertion into the male urethra with maximum effect being produced within about fifteen minutes. Both the intensity and duration of effect will be greater in patients with normal vasculature whose impotence is due to neurologic deficiency. With marked vascular damage a single drug may have incomplete action requiring additional doses or the use of a mixed drug formulation.

EXAMPLE 4

Penile inserts configured as in Example 3 are coated with a mixture of 20 μg of $PGE_1$ and 200 μg of doxazosin hydrochloride in the PEG mixture described in Example 3. Patients with moderately severe vascular deficiencies should attain erectile response from this dosage in several minutes which should be maintained for approximately thirty minutes.

EXAMPLE 5

Penile inserts configured as in Example 3 are coated with 100 μg of phenylephrine in approximately 50 mg of the PEG mixture of Example 3 or approximately 100 μg of adrenalin contained in the PEG mixture of Example 3. Inserts so fabricated are inserted into the urethra of a patient suffering from priapism, due either to pharmacological or other causes. If detumescence is not obtained within approximately five to ten minutes the application will be repeated at approximately ten minute intervals until detumescence occurs. Small incremental doses are administered in this fashion to prevent systemic overdosage when balanced circulation is reestablished.

EXAMPLE 6

Penile inserts configured as in Example 3 are coated with 100 μg of triamcinolone acetonide in approximately 50 mg of the PEG mixture of Example 3 and in 50 mg of PEG in the molecular weight range of about 2000–8000 or 50 μg of fluocinonide in approximately 50 mg of the PEG mixture of Example 3 and in 50 mg of PEG in the molecular weight range of 2000–8000. Such inserts are inserted daily into the urethra of a patient suffering from Peyronie's disease and allowed to remain in the urethra for approximately twenty minutes to provide the steroid in therapeutic local concentration in the corpus cavernosa. This method eliminates the trauma associated with the local injection of the anti-inflammatory agent which may in itself stimulate the fibrotic process which the therapeutic agent is intended to correct. If improvement is not observed after a course of treatment with single doses, multiple doses can be used for twenty minutes each until a dosage level which is effective can be established.

EXAMPLE 7

Penile inserts as in FIG. 1 are dip coated with a mixture of PEG 1450 at a temperature of 70° C. containing 1% $PGE_1$. Dipping to a depth of 2 cm in such a solution leaves a total mass of 50 mg on the distal 2 cm and contains 500 μg of $PGE_1$. The dipping time is about 1 second and cooling time 3 minutes at room temperature of about 20° C.

This system was stable when carried exposed to summer temperatures in Washington, D.C. and provided adequate lubrication upon insertion when inserted slowly over a period of approximately 5–10 seconds. Approximately 30 seconds after full insertion the system was then slowly removed over 10 seconds, the entire coating had been released into the urethra after this procedure. Erection was obtained after about 15 minutes in a normal male.

EXAMPLE 8

A penile insert configured as shown in FIG. 2 was injection molded to provide a shaft portion 12 approximately 3 cm in length having a taper from approximately 3 mm diameter at the plug end to approximately 2.5 mm at the tip end was injection molded from polyoxymethylene polymer. $PGE_1$ together with an equal weight amount of propylene glycol as a lubricant/dispersant were dissolved in ethyl alcohol at a concentration of 400 μg $PGE_1$ per 10 μl of solution. Ten μl of this solution were dispensed from a micropipette onto the shaft portion of the insert, inclined approximately 45° from the vertical, in the presence of warm, flowing air to evaporate the alcohol and provide a thin coating of the $PGE_1$ in the dispersant on the shaft of the insert. The insert was then placed within its container. The insert was inserted into the urethra and vigorously rotated and reciprocated to wipe the $PGE_1$ from the surface of the insert for approximately 20 seconds. Similar inserts were used by two other subjects and functional erections were obtained in approximately 10 minutes and lasted for approximately 30 minutes. This product exhibited a relatively short shelf life, possibly due to instability of the $PGE_1$ in the presence of moisture. It would therefore be preferred to manufacture and package the device in a low humidity or nitrogen environment.

EXAMPLE 9

A penile insert was manufactured as described in Example 8 except that the drug alprostadil ($PGE_1$) was mixed with a gamma type cyclo-dextrin at a ratio of 1 part alprostadil to 4 parts cyclodextrin. This product may have a longer shelf life than the product of Example 8.

EXAMPLE 10

Inserts configured as shown in FIGS. 1 and 2 have been evaluated in impotent males in which the impotence is associated with diabetes, post-coronary bypass (vascular insufficiency) and a post-radical prostatectomy, normal aged males and normal healthy males using various vasoactive drugs and combinations thereof. In all instances patients have responded positively although variations in intensity of erection and duration thereof were observed depending on dose, formulation and environment. Analysis of returned used systems showed residual drug loadings of from 0–50% indicating that application technique is important in use of the inserter. The preferred insertion technique which is associated with substantially complete drug removal from the inserter involves slow insertion to the maximum depth over a period of 5–10 seconds, followed by reciprocation and rotation of the inserter over approximately a 2–3 cm length while maintaining pressure on the penis to maintain intimate contact between the urethra and the shaft of the inserter for about 20 seconds and then slow removal of the inserter while maintaining compression on the penis. This technique effectively wipes the surface of the inserter clean and provides for substantially complete agent delivery.

EXAMPLE 11

An inserter configured as in FIG. 4 was injection molded to provide a shaft portion approximately 3 cm in length having a taper from approximately 3 mm diameter at the plug end to approximately 2.5 mm at the tip end provided with a 1.5 mm central bore. The plunger is inserted into the central bore to a depth that leaves a 1.5 mm long cavity at the tip. The inserter is inverted and melted PEG 1450 containing 400 μg of alprostadil is cast into the cavity and solidified therein. Upon solidification, a suppository weighing about 2.9 mg and containing about 15% wt alprostadil was formed. Alternatively, a suppository in the form of a 1.5 mm long cylinder of solid PEG 1450 containing 400 μg of alprostadil could be introduced into the shaft either at the tip or moved to the tip of inserter when the plunger is introduced into the 1.5 mm bore. The inserter is molded from polypropylene. The inserter is then placed within a polypropylene container and a sonic bond is formed between the plug portion of the inserter and the container and between the plunger which is mounted crosswise to the slot in the cap. The device may then be radiation sterilized. In use, the bonds between the plunger and the cap and the cap and the container would be broken and the inserter assembly removed from the container, the plunger would be rotated into alignment with the slot in the cap, the shaft of the inserter would be inserted into the penis up to the beginning of the plug and the plunger depressed into the slot to inject the agent load into the urethra. The device would then be removed.

EXAMPLE 12

Suppositories similar to those of Example 11 can also be formed in varying dosages to permit titration to meet the requirements of individual patients. For example, suppositories can be formed containing 100 μg, 300 μg, 500 μg and 700 μg of alprostadil dispersed in PEG 1000 or 1450 at a loading of about 15% by weight. The PEG 1000 appears to dissolve in the urethra more rapidly than the PEG 1450 and is presently the preferred PEG. The 100 μg dose is presently preferred for paraplegic patients and the 500 μg dose is presently preferred for normal patients. The 300 μg and 700 μg doses are available for titration upward or downward to meet an individual patients requirements and, if required, various combinations of these dosages could be administered sequentially to provide an even greater number of available doses. Since the density of the PEG-alprostadil formulations are about 1.1 mg/mm$^3$ the various dosages can be obtained quite simply by changing the length of the piston 29 of FIG. 4. Thus, to obtain suppositories 1.5 mm in diameter containing 100 μg, 300 μg, 500 μg and 700 μg of alprostadil, the length of the piston would be selected to form suppositories 0.375 mm, 1.125 mm, 1.875 mm and 2.625 mm in length, respectively.

EXAMPLE 13

Dosage forms comprising a mixture of the agents alprostadil and prazosin were made by depositing approximately 10 μl doses of molten PEG 1450 containing the amounts of alprostadil shown below onto the tip of an inserter having a 3 cm long shaft and allowed to cool. Thereafter approximately 10 μl doses of molten PEG 1450 containing the amounts of prazosin shown below were deposited onto the tip and allowed to cool. All inserts produced sexually functional erections in 4 different impotent subjects.

TABLE 1

| Sample # | μg Alprostadil | μg Prazosin HCl |
|---|---|---|
| 1 | 238 | 718 |
| 2 | 216 | 412 |
| 3 | 255 | 505 |
| 4 | 230 | 437 |
| 5 | 200 | 430 |

EXAMPLE 14

An inserter configured as in FIGS. 6–8 is fabricated from polypropylene in which the sleeve portion 41 is 3 cm in length and approximately 3.5 mm in external diameter having a wall thickness of about 0.3 mm. The peripheral portion 42 of the sleeve 41 is of a reduced thickness of about 0.1 mm and the thickened portion 43 is about 0.5 mm in thickness. A suppository 47, in the form of a sphere of PEG 1450 approximately 2.5 mm in diameter and containing 300 μg of alprostadil and 600 μg of prazosin, will weigh approximately 5 mg. Such device can be used in the treatment of impotence.

Having thus generally described our invention, it is obvious that various modifications will be apparent to workers skilled in the art which can be made without departing from the scope of this invention which is limited only by the following claims wherein:

We claim:

1. A composition for treating priapism and suitable for administration via the urethra, comprising, in unit dosage form, a therapeutic amount of a vasoconstrictor selected from the group consisting of epinephrine, phenylethylamine, norepinephrine, dopamine, metaraminol, phenylephrine, methoxamine, ephedrine, phenylpropanolamine, mephentermine, propylhexedrine, butoxamine, dichloroisoproterenol, propranolol, alprenolol, bunolol, nadolol, oxprenolol, penbutolol, pindolol, sotalol, timolol, metoprolol, atenolol, acebutolol, bevantolol, pafenolol, tolamolol, and combinations thereof, dispersed in a dispersant effective to facilitate delivery of the active agent through the urethra, wherein the composition is in the form of a urethral suppository, and further wherein the therapeutic amount of the vasoconstrictor is effective to treat an individual suffering from priapism when the composition is administered urethrally.

2. The composition of claim 1, wherein the dispersant is selected from the group consisting of polyethylene glycol, propylene glycol, polyvinyl pyrrolidone, polyvinyl alcohol, hydroxyalkyl celluloses, cyclodextrins, glycerol monolaurate, polyethylene glycol monolaurate, and glyceryl monolaurate.

3. The composition of claim 2, wherein the dispersant is selected from the group consisting of polyethylene glycols having molecular weights in the range of approximately 400 to 8000.

4. A composition for treating Peyronie's syndrome and suitable for administration via the urethra, comprising, in unit dosage form, a therapeutic amount of an anti-inflammatory agent selected from the group consisting of cortisone, hydrocortisone, tetrahydrocortisone, prednisone, prednisolone, methyl prednisolone, fludrocortisone, desoxycortisol, corticosterone, triamcinolone, paramethasone, betamethasone, dexamethasone, beclomethasone, salicylic acid, aspirin, diflunisal, methyl salicylate, phenylbutazone, oxyphenbutazone, apazone, phenacetin, acetaminophen, indomethacin, sulindac, mefenamic acid, meclofenamate sodium, tolmetin, ibuprofen, naproxen, fenoprofen, testosterone, and combinations thereof, dispersed in a dispersant effective to facilitate delivery of the active agent through the urethra, wherein the composition is in the form of a urethral suppository, and further wherein the therapeutic amount of the anti-inflammatory agent is effective to treat an individual suffering from Peyronie's syndrome when the composition is administered urethrally.

5. The composition of claim 4, wherein the dispersant is selected from the group consisting of polyethylene glycol, propylene glycol, polyvinyl pyrrolidone, polyvinyl alcohol, hydroxyalkyl celluloses, cyclodextrins, glycerol monolaurate, polyethylene glycol monolaurate, and glyceryl monolaurate.

6. The composition of claim 5, wherein the dispersant is selected from the group consisting of polyethylene glycols having molecular weights in the range of approximately 400 to 8000.

* * * * *